US00RE34056E

United States Patent [19]

Lindgren et al.

[11] E Patent Number: Re. 34,056

[45] Reissued Date of Patent: Sep. 8, 1992

[54] TISSUE SAMPLING DEVICE

[75] Inventors: Per G. Lindgren; Dan Akerfeldt, both of Upsala, Sweden

[73] Assignee: C.R. Bard, Inc., Murray Hill, N.J.

[21] Appl. No.: 695,451

[22] Filed: May 3, 1991

Related U.S. Patent Documents

Reissue of:

[64] Patent No.: 4,699,154
Issued: Oct. 13, 1987
Appl. No.: 890,543
Filed: Jul. 30, 1986

U.S. Applications:

[63] Continuation of Ser. No. 387,864, Jul. 31, 1989, abandoned.

[51] Int. Cl.[5] ..... A61B 10/00

[52] U.S. Cl. ..... 128/754

[58] Field of Search ..... 128/749, 751-754

[56] References Cited

U.S. PATENT DOCUMENTS

| | | | |
|---|---|---|---|
| 4,476,864 | 10/1984 | Tezel | 128/755 |
| 4,570,632 | 2/1986 | Woods | 128/751 |
| 4,600,014 | 7/1986 | Beraha | 128/754 |

FOREIGN PATENT DOCUMENTS

| | | | |
|---|---|---|---|
| 0010321 | 4/1980 | European Pat. Off. | 128/754 |
| 0141108 | 4/1980 | Fed. Rep. of Germany | 128/754 |
| SE83/00112 | 3/1983 | PCT Int'l Appl. . | |
| 175611 | 3/1966 | U.S.S.R. | 128/754 |

*Primary Examiner*—Max Hindenburg

*Attorney, Agent, or Firm*—Jones, Askew & Lunsford

[57] ABSTRACT

A device for tissue sampling by thick needle punctuation including a needle assembly including a hollow first needle and second needle extending through the hollow first needle. The needle assembly is contained in a housing having an opening through which the needles extend. Compressed springs in the housing are caused to expand to urge the needles away from the housing during the sampling of tissue. A rod is provided extending from the housing to simultaneously place the springs in a compressed condition.

23 Claims, 2 Drawing Sheets

TISSUE SAMPLING DEVICE

Matter enclosed in heavy brackets [ ] appears in the original patent but forms no part of this reissue specification; matter printed in italics indicates the additions made by reissue.

*This application is a continuation of Ser. No. 07/387,864 filed Jul. 31, 1989, now abandoned, which is a reissue of 06/890,543 filed Jul. 30, 1986 U.S. Pat. No. 4,699,154.*

FIELD OF THE INVENTION

The present invention relates to a device for tissue sampling by means of what is generally termed thick needle punctuation. In particular the invention relates to a device for propelling and operating a needle assembly, used for such sampling.

BACKGROUND OF THE INVENTION

Sampling of inner tissue on humans and animals, so called biopsy, has become increasingly common. Using thick needle punctuation one can for example take out samples from deeply located organs, such as the liver or the kidneys. This kind of sampling, which is a very mild treatment, is usually carried in such a way that a doctor inserts a needle assembly through the skin and to the desired sampling location. The needle assembly comprises a hollow outer needle and a therewithin slidably provided inner needle. The inner needle has a pointed front portion, and is near the point provided with a hollow for receiving the tissue sample. The sampling itself is carried out in such a way that the inner needle is first pressed slightly inwards from the initial position, such that the surrounding tissue expands into the hollow provided in the inner needle. Thereafter the hollow outer needle is pushed forward to cover the inner needle thus cutting out a tissue sample, which thereby is connected in the hollow provided in the inner needle, and retained by the surrounding outer needle. Then the entire needle assembly containing the collected tissue sample is withdrawn, whereafter the sample can be taken out and analyzed. The sampling procedure is commonly monitored using ultra sonic equipment, to ensure the sampling is carried out correctly.

Such sampling is mostly carried out completely manually, demanding that two doctors participate, one of whom operates the ultra sonic equipment, and the other carrying out the sampling, i.e. a very work intensive procedure. In addition the sampling demands great skill and precision when handling the needle assembly, especially for coordinating the movements of the two needles, such that the entire needle assembly is first brought to the desired initial position, whereafter the inner needle is pushed forward and finally that the outer needle is moved forward over the inner needle, simultaneously cutting off the tissue sample. It can easily happen that the inner needle inadvertently is withdrawn during the cutting phase, with the consequence that none or too small an amount of tissue is collected in the hollow in the inner needle.

Thus there is a great need for biopsy devices, demanding the participation of just one doctor, and enhancing the security when operating the needle assembly. An attempt to solve this problem is described in Se-A-No. 8202061-1, with the same applicants as the present application, the inventive idea of which resides in placing the needle assembly in a box, in which box there are provided propelling means for propelling the outer and inner needles, such that they carry out the above mentioned coordinated movements when the needle assembly has been located to the correct sampling position in the body. The needles are brought to carry out the desired movements in that the operator actuates a release mechanism outside of the box.

This known device constituted a great technical progress, since it made possible both one-hand operation during sampling (the doctor could manipulate the ultra sonic equipment with one hand and the sampling device with the other hand), and also enchanced security and precision when sampling (the relative movements of the needles were automatically controlled by the device). In spite of this the known device has shown several drawbacks. Among other things it has certain deficiencies regarding stability, and the procedures for placing the propelling means for the needles under tension and for loading the needle assembly, are relatively complicated and are being carried out in separate steps, whereby the propelling means must be tightened manually or with the aid of special tools. Further, the known device is deficient concerning security (e.g. there is a risk for inadvertent release of the device), and guiding of the needle assembly.

OBJECT OF THE INVENTION

The object of the invention is to provide an improved tissue sampling device of the type described, which device is better than previously known devices, and fulfills the demands that in practice are placed on this type of devices. A special object of the invention is to provide a tissue sampling device of said type, which device is more stable and has a longer life. Another particular object of the invention is to provide such a device, being simpler and safer to load, to operate and to release than previously known devices of this kind. A further special object of the invention is to enhance security in this said type of tissue sampling device, especially by making possible simple control of whether the device is loaded or not, to prevent inadvertent release of the loaded device, and to prevent undesired rotation of the needle assembly. These and other objects of the invention will be apparent from the following description of preferred embodiments of the invention, whereby special features of said embodiments are disclosed in the appended patent claims.

DESCRIPTION OF PREFERRED EMBODIMENTS

In the following a detailed description of some at present preferred embodiments of the invention will be given with reference to the drawings. However, the invention is not to be considered as restricted to these embodiments, but many modifications and variations can be made within the scope of the following patent claims.

Figure 1A:
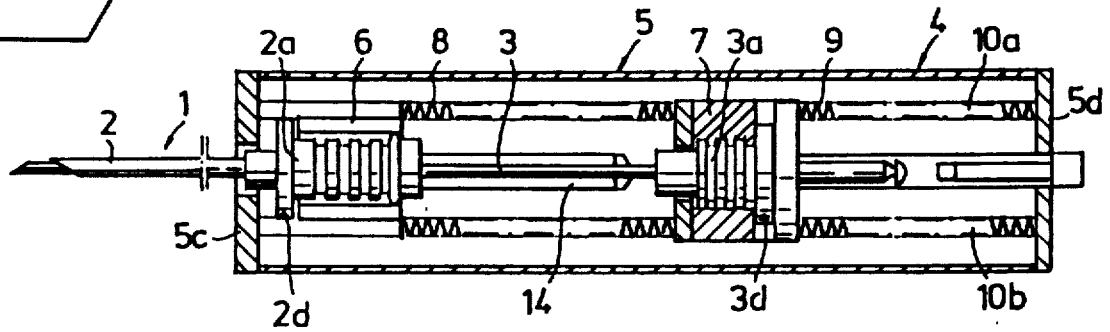
FIGS. 1A-1C show schematic top views of a tissue sampling device according to the invention comprising a needle assembly, said assembly being shown in three different positions during sampling.
Figure 1B:
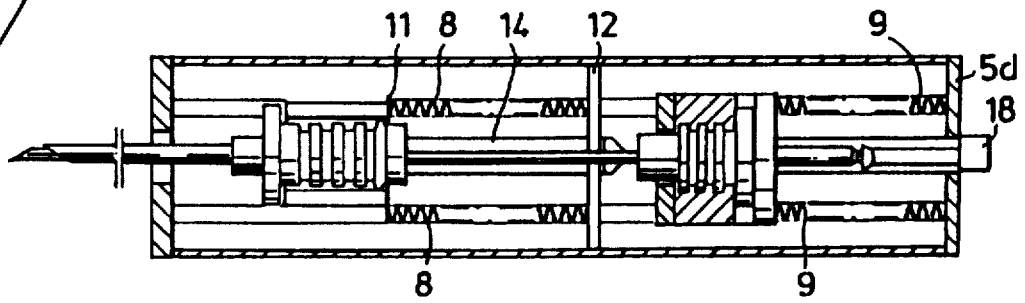
Figure 1C:
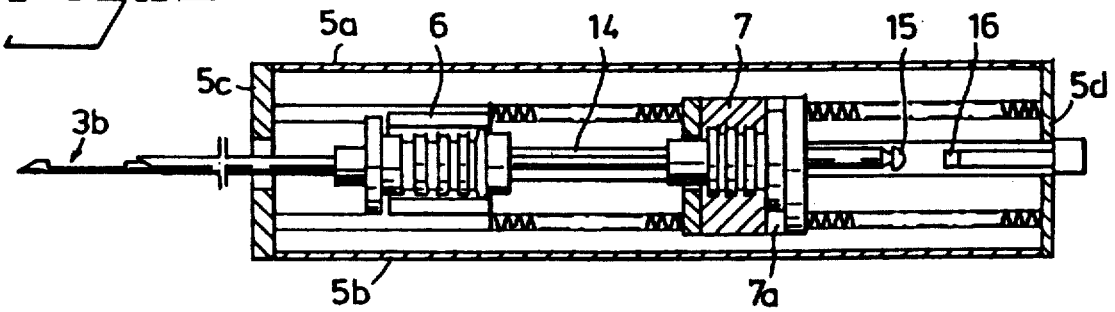

FIGS. 1A-1C schematically show how a needle assembly 1 is prepared for and manipulated for tissue sampling with the device according to the invention. The needle assembly 1 comprises a hollow outer needle 2 and an inner needle 3. The needles 2, 3 are pointed at one end, and the inner needle 3 is also provided with a hollow 3b at the point, for receiving the sample. At the opposite end the needles 2, 3 are provided with heads 2a and 3a respectively, for mounting within the sampling device according to the invention, which is generally designated with 4. In this schematically shown embodiment, the device 4 comprises a box-shaped housing 5, comprising side walls 5a and 5b, as well as front and rear end walls 5c, 5d. A front side 6 and a rear side 7 are slidably provided in the longitudinal direction of the housing 5. Each slide 6 and 7 respectively is being actuated by at least one spring 8 and 9 respectively, pressing said respective slide towards the position shown in FIG. 1A. The spring 8 acts a stop 11 provided on the slide 6 and a fixed transverse wall 12 in the housing 5 (see FIG. 1B). The spring 9 acts between a stop on the slide 7 and the rear end wall 5d in the housing 5. In the housing 5 there are two parallel slide bars or guide rods 10a, 10b, on which the slides 6, 7 run.

The front slide 6 may be retained in a withdrawn position by means of a hook provided on a tongue member 14 protruding from the slide, said tongue member engaging the bottom edge of the transverse wall 12. The rear slide 7 may in a corresponding way be hooked and retained in a withdrawn position by means of a hook means 15 protruding from the slide, said means engaging a springy hook member 16 at the rear wall 5d of the housing 5.

The tissue sampling device shown in FIG. 1A-C is loaded and released in the following manner. FIG. 1A shows the unloaded initial position, in which position the slides 6, 7 are being pressed leftwards (to the left) in FIG. 1A, i.e. against the front end wall 5c of the housing 5 and against the transverse wall 12 respectively, by the springs 8 and 9 respectively. The needle assembly 1, in which the inner needle 3 is freely slideable in the hollow outer needle, is placed in its correct position in the housing 5, so that each needle head 2a, 3a follows the movements of the slides 6, 7 respectively. In the shown embodiment this is achieved in that the needle head 2a rests in the generally U-shaped slide 6, and surrounds said slide with a front flange 2d and rear flange (not shown), whereas the needle head 3a is provided with a flange 3d, resting in a transverse recess 7a on the slide 7.

Thus when the needle assembly 1 has been placed in the device, the device is energized in that the slides 6 and 7 are moved simultaneously to the position shown in FIG. 1B by the operator, whereby the springs 8, 9 are compressed and acts to return the slides 6, 7 to the initial position(the energizing device itself is not shown in FIGS. 1A—C in order that the drawings be clear, but it will be described in connection with FIGS. 2 and 3). The slides 6, 7 are retained in the energized position according to FIG. 1B by means of the above mentioned hook mechanisms 12, 14-16. The needle assembly 1 may now be transferred to the desired sampling position in the body.

When the needle assembly has been positioned at the correct location in the body the sampling is carried out by pressing a release button 18 whereby the engagement between the hook means 15, 16 is interrupted. Because of the biased spring 9, the slide 7 together with the inner needle 3, is pushed to the left towards the initial position. The slide 5, together with the outer needle 2, is still retained in the energized position, whereby the inner needle 3 protrudes from the outer needle, thereby exposing the hollow 3b. This position is shown in FIG. 1C, in which the slide 7 has not fully reached its initial position at transverse wall 12. Immediately after having reached the position shown in FIG. 1C, the slide 7 impacts and abuts the hook spring 14, and interrupts the engagement of said hook with the transverse wall 12, whereby the spring 8 also pushes back the slide 6 to its initial position according to FIG. 1A. Thereby the outer needle 2 again is pushed over the hollow 3b in the inner needle, thereby cutting the tissue sample that is being collected in the hollow 3b. Thereafter the needle assembly 1 is removed from the sampling device and the sample is analyzed.

Having described the major functions of the sampling device and its cooperation with the needle assembly, a preferred embodiment of the tissue sampling device will now be described in more detail, with reference to FIGS. 2 and 3 in the drawings, where corresponding details are provided with the same reference numerals as in FIGS. 1A—1C.

Figure 2:
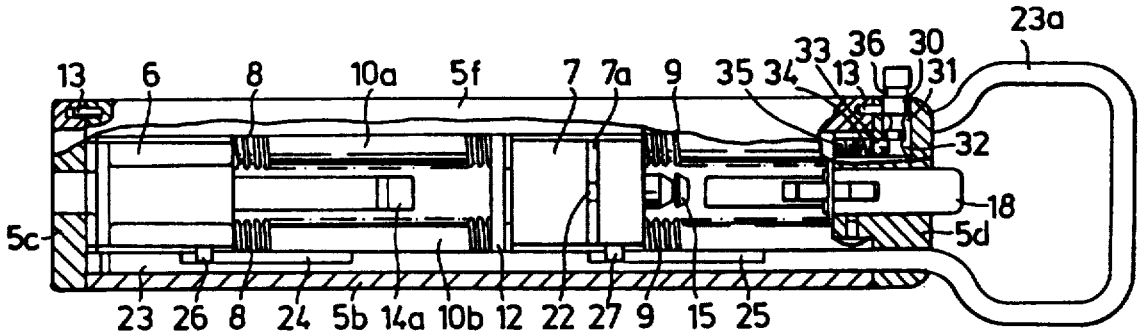
FIG. 2 shows a top view of a preferred embodiment of the tissue sampling device according to the invention, partly broken away.
Figure 3:
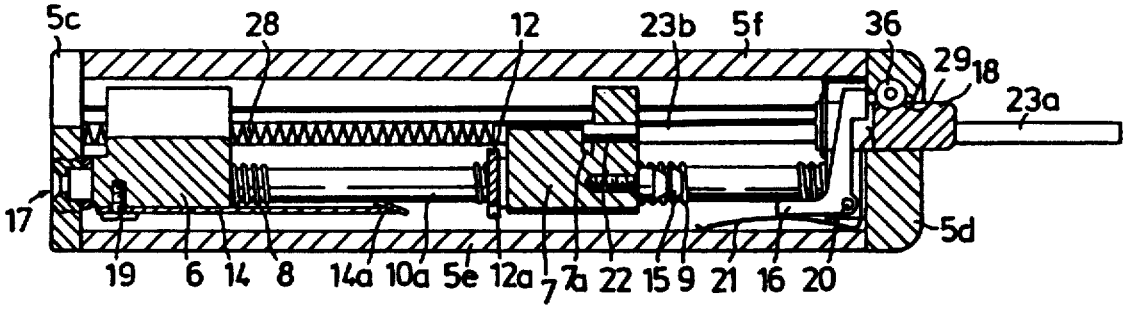
FIG. 3 shows a longitudinal sectional view of the tissue sampling device according to FIG. 2.

FIGS. 2 and 3 show a tissue sampling device according to the invention in the position according to FIG. 1A, and for reasons of clarity the needle assembly has been excluded from these figures. It is shown how the housing 5, in addition to the side walls 5a, 5b and the end walls 5c, 5d, is also provided with a bottom 5e and a cover 5f. The latter is openable, so that the needle assembly 1 can be inserted in and removed from the device. For this purpose the cover may rest on the end walls 5c, 5d, as illustrated by the pins 13 in FIG. 2. A cover is conveniently kept in closed position by means of some suitable (not shown) locking mechanism, e.g. a snap-lock. The slide bars 10a, 10b, on which the slides 6 and 7 run, are in the shown embodiment mounted on the end walls 5c, 5d, e.g. by means of screw and gasket, as is illustrated at 17 in FIG. 3, said slide bars having a circular cross-section. The slides 6, 7 are provided with corresponding cooperating means, so that they can be supported by and slide along the slide bars 10a, 10b. It is preferred that the slides 6, 7 for this purpose are provided with through-bores adapted to the cross-sectional shape of the slide bars 10a, 10b. The arrangement with slide bars common to both slides 6, 7, especially with two parallel slide bars placed on each side of the slides, gives significant advantages, i.a. very good stability and precision when manipulating the needle assembly, only slight wear of the elements of the device etc.

The propelling springs 8, 9 are coil springs, being arranged around the slide bars 10a, 10b respectively, and act as compressive springs, making them develop a very suitable, uniform and symmetric driving force for propelling the slides 6, 7 and the needle assembly 1.

FIG. 3 shows most clearly the preferred design of the spring block 14, here in the shape of a slightly upwardly biassed leaf spring, one end of which being shaped as a hook 14a, or forming a functionally analogous stop surface. A spring 14 is attached to the bottom of the slide 6 by means of a screw 19. A transverse wall 12 (which also functions as a bucker for the springs 8) cooperating with a spring 14, is provided with a lower groove 12a, through which the hook 14a passes when the slide 6 is moved backwards on energizing, whereafter said hook is sprung upwards and engages the lower rear edge of the transverse wall 12, thereby preventing the slide 6 from returning to the initial position. The hook 14a is retained in this position until the slide 7 when returning to its initial position impacts the hook 14a pressing it downwards, in such a way that its engagement with the transverse wall 12 is interrupted. FIGS. 2 and 3 also show a preferred design of the retaining mechanism for the slide 7. The hook member 15, mounted in the slide 7, has in this embodiment the shape of a frusto-conical head, a straight base edge of which is engageable with the hook mechanism 16, said mechanism being generally L-shaped, and being pivotably journalled on a pivot 20 at its corner, and whereby one leg of said L-shaped element is connected with the release button 18. A bent leaf spring 21 biasses the hook 16 upwards (and the release button 18 outwards). When the device is energized the hook 16 retains the slide 7 in an energized position, through engagement with the hook member 15. When performing a sampling the push button 18 is pressed, whereby the hook 16 is moved downwards, so that the engagement with the hook 15 is interrupted and the slide 7 is returned to its initial position.

It is important that rotation of the needle assembly is prevented during sampling, and FIGS. 2 and 3 show a special device for preventing rotation of the inner needle 3. As mentioned in connection with FIGS. 1A—C the head 3a of the inner needle can advantageously be provided a flange 3d, engaging a transverse recess 7a on the slide 7. This flange 3d is preferably provided with a slit, cooperating with a guide pin 22, provided in or over said transverse recess 7a. This arrangement prevents undesired rotation of the inner needle 3.

An essential feature of the sampling device according to the invention is that it is provided with an energizing mechanism, biassing both propelling springs 8, 9 simultaneously and without the need of special tools. In the shown preferred embodiment the energizing mechanism comprises an energizing rod 23, running in a longitudinal guide in the housing 5, e.g. in its side wall 5b. The rod 23 is provided with slits 24 and 25, cooperating with protrusions 26 and 27 on the slides 6, 7 respectively. The energizing rod 23 runs through the end wall 5d, forming outside said wall a handle 23a. The operator energizes the sampling device by pulling the handle 23a, whereby the protrusions 26, 27 are brought into engagement with the front edges of the slits 24, 25 respectively, and whereby the slides 6, 7 are moved towards the energized position (FIG. 1B). The slides 6, 7 are locked in this position in that the hook spring 14 is brought into engagement with the transverse wall 12 and in that the spring biased hook 16 engages the hook means 15.

The free end of the handle 23a preferably continues with a second rod-shaped portion 23b, running in one piece in a second longitudinal guide in the housing 5, e.g. the side wall 5a. A return spring 28, acting between the rod element 23b and the housing, returns the energizing mechanism to its initial position, when the slides 6, 7 have been locked still in the energized position. For this purpose the slits 24, 25 are at least as long as the stroke of the slides between the initial position and the energized position. By this return action the handle 23b requires little space during the sampling, and it also enhances security, since the operator can easily control whether the device is energized or not (the return spring has considerably less force than the energizing spring 8, 9).

A tissue sampling device according to the invention is preferably also provided with a securing mechanism, preventing inadvertent release. In the shown embodiment the release button 18 is provided with a groove 29 in the shape of a circular segment, cooperating with a transversely running securing pin 30, which in its turn runs in a corresponding circular transverse bore in the end wall 5d.

The pin 30 is provided with two peripherally located recesses 31 and 32, cooperating with a ball 33 inserted in a bore in the end wall 5d, said ball being pressed against the pin by means of a spring 34, 35 designates a screw, retaining the spring in the bore. The pin 30 is also provided with a third peripherally located recess 36, cooperating with a groove 29 in the release button 18. In the shown position the ball 33 is engaged with the peripherally located recess 32, said recess 36 at the same time being located immediately above the release button 18, i.e. the pin 30 does not prevent sampling to be carried out by pressing the button.

By pressing the pin 30, inwards, thus overcoming the force from the spring 34, the ball 33 can be brought to a secured position in which it bears against the peripherally located recess 31. In this position there is no recess in the pin at the groove 29 in the release button 18, and thus the pin engages the groove thereby preventing pressing of the button 18 inwards. In this way one can easily and safely switch the sampling device between locked and unlocked position. The pin 30 is suitably arranged in such a way that it in the unlocked position protrudes from the housing 5 on one side (FIG. 2), while its other end protrudes from the opposite side in the locked position. The ends of the pins are preferably provided with different colours on respective protruding ends, e.g. red colour 36 indicating unlocked position and green colour on the opposite end indicating locked position.

As mentioned above the invention is not restricted to the above described and in the drawings specifically shown embodiments, and it is for one skilled in the art obvious that the invention can be varied and modified in many ways within the scope of the appended patent claims. One can for example use another number or another type of spring means than those particularly described, and the same applies to many other constructive details, e.g. the different hook mechanisms described.

I claim:

1. A tissue sampling device comprising:

a housing having a longitudinal axis extending from a first housing end to a second housing end, said first housing end having a first opening and said second housing end having a second opening;

a hollow first needle positioned within said housing and extendable from said first opening, said hollow first needle being moveable along said axis;

a second needle extending through said hollow first needle and moveable along said axis, said second needle having a pointed end which is extendable from said hollow first needle and said first opening, and including a tissue sample receiving recess;

a first slide coupled to said hollow first needle and positioned within said housing for movement along said axis to thereby move said hollow first needle along said axis;

a second slide coupled to said second needle and positioned within said housing for movement along said axis to thereby move said second needle along said axis;

first power means positioned within said housing in contact with said second slide for storing energy in a compressed mode and releasing energy in an expanded mode, said first power means being expandable to urge said second slide along said axis towards said first opening causing said pointed end to be extended from said hollow first needle so that a tissue sample can be captured within said recess;

second power means positioned within said housing in contact with said first slide for storing energy in a compressed mode and releasing energy in a expanded mode, said second power means being expandable to urge said first slide along said axis towards said first opening causing said hollow first needle to be extended from said first opening so that said recess of said second needle is enclosed by said hollow first needle;

a first latch means positioned within said housing and extending out of said second opening for releasably holding said first power means in said compressed mode;

a second latch means positioned within said housing for releasably holding said second power means in said compressed mode and being releasable in response to and subsequent to release of said first power means; and, energizing means extending through said second housing end into said housing and being operably coupled to said first slide and said second slide and moveable along said axis for moving said first slide and said second slide along said axis towards said second housing end for simultaneously causing said first latch means to hold said first power means in said compressed mode and said second latch means to hold said second power means in said compressed mode.

2. Device according to claim 1 wherein said first slide and said second slide are slidably supported within said housing on at least one guiding rod, said rod being mounted in said housing and extending in the direction of said longitudinal axis.

3. Device according to claim 2 including two parallel of said guiding rods extending through said first slide and said second slide.

4. Device according to claim 1 wherein said first power means is a spring and said second power means is a spring.

5. Device according to claim 2 wherein said first power means is a first coil spring which is coiled around said at least one guiding rod and is positioned between said first slide and a first fixed bucker positioned within said housing between said first slide and said second slide, and wherein said second power means is a second coil spring which is coiled around said at least one guiding rod and is positioned between said second slide and a second fixed bucker positioned within said housing between said second slide and said second housing end.

6. Device according to claim 1 further including spring means positioned within said housing for urging said energizing means towards said first housing end after said first latch means is caused to hold said first power means in said compressed mode and said second latch means is caused to hold said second power means in said compressed mode.

7. Device according to claim 1 wherein said first latch means includes a release device extending out of said second opening and further including locking means operable from outside of said housing for locking said release device in a first position and unlocking said release device in a second position.

8. Device according to claim 1 wherein at least one of said first slide and said second slide includes a guide pin extending in the direction of said axis and cooperating with a slit in a corresponding one of said hollow first needle and said second needle for preventing rotation of said needle.

*9. A biopsy needle for use with a tissue sampling device having a housing, a first slide mounted for longitudinal motion within said housing, and a second slide having a transverse recess formed therein and being mounted for longitudinal motion within said housing, said biopsy needle comprising:*

*a hollow first needle having proximal and distal ends;*

*a second needle extending through said hollow first needle and freely slidable therewithin, said second needle having proximal and distal ends;*

*a first head mounted to said proximal end of said first needle, said first head having front and rear flanges formed thereon in spaced-apart relation for receiving said first slide therebetween, such that when said first head is placed on said first slide, said slide is mateingly received between said front and rear flanges to couple said first needle to said first slide; and*

*a second head mounted to said proximal end of said second needle, said second head having a flange thereon dimensioned to be received within said transverse recess of said second slide such that when said second head is placed on said second slide, said flange on said second head engages said transverse recess in said second slide to couple said second needle to said second slide.*

*10. The biopsy needle of claim 9, wherein said second slide further includes a guide pin projecting across said transverse recess, and wherein said flange on said second head further comprise a slit dimensioned to receive said guide pin therewithin such that when said flange on said second head engages said transverse recess in said second slide, said guide pin is received within said slit to prevent rotational movement of said second needle with respect to said second slide.*

*11. The biopsy needle of claim 9, wherein said second needle further comprises a tissue sampling recess formed adjacent said distal end thereof.*

*12. A biopsy needle for use with a tissue sampling device having a housing, a first slide mounted for longitudinal motion within said housing, and a second slide having a transverse recess formed therein with a guide pin projecting across said transverse recess, said second slide being mounted for longitudinal motion within said housing, said biopsy needle comprising:*

*a hollow outer needle having proximal and distal ends;*

*an inner needle extending through said hollow outer needle and freely slidable therewithin, said inner needle having a proximal end, a pointed distal end, and a tissue sampling recess formed adjacent said distal end;*

*a first head mounted to said proximal end of said outer needle, said first head having front and rear flanges formed thereon in spaced-apart relation for receiving said first slide therebetween such that when said first head is placed on said first slide, said slide is mateingly received between said front and rear flanges to couple said outer needle to said first slide; and*

*a second head mounted to said proximal end of said inner needle, said second head having a flange thereon dimensioned to be received within said transverse recess of said second slide, said flange defining a slit dimensioned to receive said guide pin therein such that when said second head is placed on said second slide, said flange on said second head engages said transverse recess in said second slide and said guide pin is received within said slit to couple said inner needle to said second slide and to prevent rotational movement of said inner needle.*

13. A tissue sampling device comprising:

*a housing having a longitudinal axis extending from a first housing end to a second housing end, said first housing end having an opening therethrough;*

*a hollow first needle positioned within said housing and extendable from said opening, said hollow first needle being moveable along said axis;*

*a second needle extending through said hollow first needle and moveable along said axis, said second needle having a pointed end which is extendable from said hollow first needle and said opening and including a tissue sample receiving recess;*

*a first slide coupled to said hollow first needle and positioned within said housing for movement along said axis thereby to move said hollow first needle along said axis;*

*a second slide coupled to said second needle and positioned within said housing for movement along said axis thereby to move said second needle along said axis;*

*first power means positioned within said housing in contact with said second slide for storing energy in a compressed mode and releasing energy in an expanded mode, said first power means being expandable to urge said second slide along said axis towards said opening causing said pointed end of said second needle to be extended from said hollow first needle so that a tissue sample can be captured within said recess;*

*second power means positioned within said housing in contact with said first slide for storing energy in a compressed mode and releasing energy in an expanded mode, said second power means being expandable to urge said first slide along said axis towards said opening causing said hollow first needle to be extended from said opening so that said recess of said second needle is enclosed by said hollow first needle;*

*a first latch means positioned within said housing and releasable from without said housing for releasably holding said first power means in said compressed mode;*

*a second latch means positioned within said housing for releasably holding said second power means in said compressed mode and being releasable in response to and subsequent to release of said first power means; and*

*energizing means actuatable from without said housing and being operably coupled to said first slide and said second slide and moveable along said axis for moving said first slide and said second slide along said axis towards said second housing end for simultaneously causing said first latch means to hold said first power means in said compressed mode and said second latch means to hold said second power means in said compressed mode.*

*14. Device according to claim 13 wherein said first slide and said second slide are slidably supported within said housing on at least one guiding rod, said rod being mounted in said housing and extending in the direction of said longitudinal axis.*

*15. Device according to claim 14 including two parallel of said guiding rods extending through said first slide and said second slide.*

*16. Device according to claim 13 wherein said first power means is a spring and said second power means is a spring.*

*17. Device according to claim 14 wherein said first power means is a first coil spring which is coiled around said at least one guiding rod and is positioned between said first slide and a first fixed bucker positioned within said housing between said first slide and said second slide, and wherein said second power means is a second coil spring which is coiled around said at least one guiding rod and is positioned between said second slide and a second fixed bucker positioned within said housing between said second slide and said second housing end.*

*18. Device according to claim 13 further including spring means positioned within said housing for urging said energizing means towards said first housing end after said first latch means is caused to hold said first power means in said compressed mode and said second latch means is caused to hold said second power means in said compressed mode.*

*19. Device according to claim 13 wherein said first latch means includes a release device extending out of said second opening and further including locking means operable from outside of said housing for locking said release device in a first position and unlocking said release device in a second position.*

*20. Device according to claim 13 wherein at least one of said first slide and said second slide includes a guide pin extending in the direction of said axis and cooperating with a slit in a corresponding one of said hollow first needle and said second needle for preventing rotation of said needle.*

*21. A biopsy needle for use with a tissue sampling device having a housing with a forward end, a first slide mounted for longitudinal motion within said housing, and a second slide mounted for longitudinal motion within said housing, said biopsy needle comprising:*

*a hollow first needle having proximal and distal ends;*

*a second needle extending through said hollow first needle and freely slidable therewithin, said second needle having proximal and distal ends;* a first head mounted to said proximal end of said hollow first needle, said first head including first flange means associated therewith for coupling said hollow first needle to said first slide for longitudinal motion both toward and away from said forward end of said housing; and

*a second head mounted to said proximal end of said second needle, said second head including second flange means associated therewith for coupling said second needle to said second slide for longitudinal motion both toward and away from said forward end of said housing.*

*22. The biopsy needle of claim 21, wherein said first flange means associated with said first head comprises front and rear flanges formed on said first head in spaced-apart relation for receiving said first slide therebetween so as to couple said hollow first needle to said first slide for longitudinal motion both toward and away from said forward end of said housing.*

*23. The biopsy needle of claim 21, wherein said second flange means associated with said second head comprises a flange formed on said second head and dimensioned to be received within a transverse recess formed in said second slide so as to couple said second needle to said second slide for longitudinal motion both toward and away from said forward end of said housing.*

* * * * *